United States Patent
Schloemer et al.

(12)

(10) Patent No.: US 6,376,717 B2
(45) Date of Patent: Apr. 23, 2002

(54) PREPARATION OF ASTAXANTHIN

(75) Inventors: George C. Schloemer, Longmont; Jeffery L. Davis, Berthoud, both of CO (US)

(73) Assignee: Prodemex, S.A. de C.V., Sinaloa (MX)

( * ) Notice: Subject to any disclaimer, the term of this patent is extended or adjusted under 35 U.S.C. 154(b) by 0 days.

(21) Appl. No.: 09/813,685

(22) Filed: Mar. 19, 2001

Related U.S. Application Data

(60) Provisional application No. 60/199,875, filed on Apr. 26, 2000.

(51) Int. Cl.[7] .................................................. C07C 45/45
(52) U.S. Cl. ........................ 568/347; 568/348; 568/362; 568/374
(58) Field of Search ................................ 568/347, 348, 568/362, 374

(56) References Cited

U.S. PATENT DOCUMENTS 4,212,827 A * 7/1980 Paust et al.
5,625,099 A * 4/1997 Ernst et al.

* cited by examiner

*Primary Examiner*—Johann Richter
*Assistant Examiner*—Sikarl A. Witherspoon
(74) *Attorney, Agent, or Firm*—Knobbe, Martens, Olson & Bear, LLP

(57) ABSTRACT

The present invention provides a method for preparing astaxanthin from zeaxanthin. Specifically, the present invention provides a method for said conversion using a halogenating agent with the salt of chloric or bromic acid in an inert solvent.

25 Claims, No Drawings

PREPARATION OF ASTAXANTHIN

This application claims the benefit of provisional application 60/199,875 filed Apr. 26, 2000.

BACKGROUND OF THE INVENTION

1. Field of the Invention

The present invention relates to a process for preparing astaxanthin. Specifically, the process of the present invention demonstrates a novel conversion of zeaxanthin directly to astaxanthin. The invention can be accomplished in either one chemical step or in a sequence of two chemical steps.

2. Description of the Related Art

In nature, the reddish color of meat of anadromous fish such as salmon or sea trout and lobsters is due to red pigments such as astaxanthin, which is present in naturally occurring feeds such as crustaceans and other related astaxanthin containing species. Commercially, astaxanthin is an economically important natural carotenoid which is extensively used in aquaculture to induce natural color in certain species of fish, as the fish do not have access to these natural pigmentation sources. In addition, related xanthophylls are used as a food additive to enhance the yolk color of eggs in the poultry industry.

Astaxanthin isolated from crustacean wastes or produced synthetically have been used as constituents in fish feed. However, the synthetic manufacture of astaxanthin and the process for manufacture of natural astaxanthin are expensive and tedious. In particular, the material is prepared either by total synthesis, by algae culture or by bacterial fermentation (See, for example, U.S. Pat. Nos. 6,022,701, 6,015,684, 5,972,642 and 5,935,808). Manufacture by total synthesis is very laborious and costly, and invariably provides a complete mixture of isomers that are not normally found in nature. Likewise, the culturing of algae and the fermentation of bacteria only produce low yields of the desired product. In addition, these methods are tedious and very costly.

reported that dimethylzeaxanthin could be converted to dimethylastaxanthin, but the removal of the methyl groups could not be accomplished to produce astaxanthin (Surmatis and Tommen, *J. Org. Chem.* (1967) 32: 180). In fact, conversion reactions of this type are known to be very difficult and invariably result in the formation of further oxidation products (Cooper et al, *J. C. S. Perkins I* (1975) 2195). A large number of researchers have described the total synthesis of related carotenoids such as astaxanthin, but no attempts have been made for the conversion of one such carotenoid to another. Workers at BASF have demonstrated the conversion of beta-carotene to canthaxanthin by an oxidation process similar to the process described herein, but no attempts have been made to convert zeaxanthin to astaxanthin (U.S. Pat. No. 4,212,827).

Zeaxanthin can be obtained directly from natural sources or it can be prepared in good yields from lutein by previously describe methods (See Rodriguez, U.S. Pat. No. 5,973,211).

Therefore, it is evident that there is a need for an efficient industrial-scale method to convert readily available zeaxanthin to astaxanthin.

SUMMARY OF THE INVENTION

The present invention relates to method for preparing astaxanthin from zeaxanthin or 3,3',4,4'-tetrahydroxy-β-carotene, which includes contacting the zeaxanthin or 3,3',4,4'-tetrahydroxy-β-carotene with a halogenating agent in the presence of chloric or bromic acid or salts thereof Preferably, the halogenating agent is selected from the group including N-bromosuccinimide, bromine, pyridinium tribromide, iodine, and mixtures thereof either added directly or generated in situ with a compound selected from the group including sodium bromide, potassium bromide, sodium iodide and potassium iodide. The disclosed method may further include a reaction solvent system, wherein said reaction solvent is selected from the group including an organic solvent and water. In a preferred embodiment, the

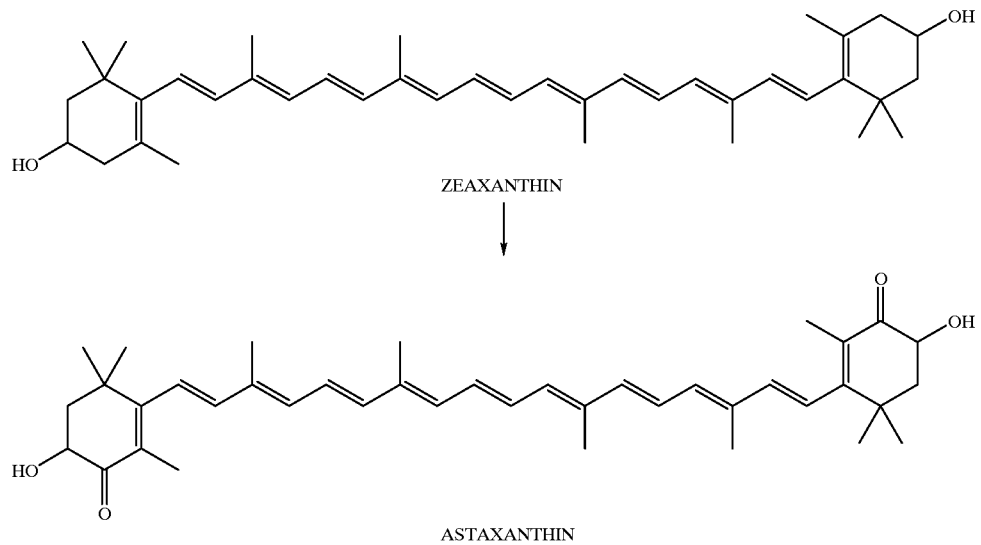

ZEAXANTHIN

↓

ASTAXANTHIN

In spite of the natural and abundant availability of zeaxanthin coupled with the significant economic value of astaxanthin, surprisingly, the direct conversion of zeaxanthin to astaxanthin has not been described. It has been organic solvent is chloroform. In a more preferred embodiment, the halogenating agent is N-bromosuccinimide or pyridinium tribromide.

In a preferred embodiment, the halogenating agent is generated in situ from a mixture of an oxidizing agent and a compound selected from the group consisting of potassium bromide, sodium bromide, sodium iodide and potassium iodide. Preferably, the oxidizing agent is selected from the group including bromic acid, chloric acid and salts thereof and preferably, the mixture is acidic. In a most preferred embodiment, when the halogenating agent is generated in situ, the mixture includes a solution of sodium bromate and potassium bromide. In an alternate most preferred embodiment, the halogenating agent is generated in situ from a mixture which includes a solution of sodium iodine and sodium chlorate.

The present disclosure also relates to a method for preparing 3,3',4,4'-tetrahydroxy-β-carotene from zeaxanthin, which includes contacting said zeaxanthin with a halogenating agent to form a mixture followed by contacting said mixture with a base. In a most preferred embodiment, the halogenating agent is N-bromosuccinimide and the base is an amine base. In an alternate preferred embodiment, the halogenating agent is selected from the group including N-bromosuccinimide, bromine, pyridinium tribromide, iodine, and mixtures thereof either added directly or generated in situ with a compound selected from the group including sodium bromide, potassium bromide, sodium iodide and potassium iodide. The method may further include a reaction solvent system, wherein the reaction solvent is selected from the group including an organic solvent and water. In a preferred embodiment, the organic solvent is chloroform. In a preferred embodiment of the method, the halogenating agent is N-bromosuccinimide and the amine base is N,N-diisopropylethylamine.

The present invention also relates to a method for preparing astaxanthin from 3,3',4,4'-tetrahydroxy-β-carotene, which includes contacting said 3,3',4,4'-tetrahydroxy-β-carotene with a mixture which includes a halogenating agent and an acid selected from the group including bromic acid, chloric acid and salts thereof. In a preferred embodiment, the halogenating agent is N-bromosuccinimide. The method may further include a reaction solvent system, wherein the reaction solvent is selected from the group including an organic solvent and water. In a preferred embodiment, the organic solvent is chloroform. In a preferred embodiment of the method, the halogenating agent is generated in situ from a mixture of an oxidizing agent and a compound selected from the group including potassium bromide, sodium bromide, sodium iodide and potassium iodide. In a most preferred embodiment the oxidizing agent is selected from the group including bromic acid, chloric acid, and salts thereof. In a preferred embodiment, the mixture is acidic. In a most preferred embodiment, when the halogenating agent is generated in situ, the mixture includes solutions of sodium bromate and potassium bromide. In an alternate most preferred embodiment, the mixture for generating the halogenating agent in situ includes solutions of sodium iodine and sodium chlorate.

DETAILED DESCRIPTION OF THE PREFERRED EMBODIMENT

The present invention is directed to a method of treating zeaxanthin with oxidizing agents. Non-limiting examples of performing allylic oxidations or agents that may be employed in oxidation reactions have been reviewed in Barry M. Trost, Ed. and Ian Fleming, Ed. "*Comprehensive Organic Synthesis,*" Volume 7, Pergamon Press, New York, 1991, pages 83–117, and Richard C. Laro "*Comprehensive Organic Transformations,*" Wiley-VCH, New York, 1999, pages 1207–1209, which are incorporated herein in their entirety by reference. Preferably, the oxidizing agent is a halogenating agent in the presence of salts of chloric or bromic acids or salts of chlorate or bromates. More preferably, the halogenating agent is selected from the group consisting of N-bromosuccinamide, bromine, pyridinium tribromide, iodine, sodium iodide and mixtures thereof or generated in situ from metal bromides or iodides. Still more preferably, the halogenating agent is N-bromosuccinimide or pyridinium bromide per bromide ($C_5H_5NH^+Br_3^-$) in the presence of sodium chlorate. Also, preferably, the oxidizing (halogenating) agent is generated in situ from a mixture of acidic sodium bromate and potassium bromide solutions.

In one embodiment, the allylic oxidation reaction can be carried out in a single step.

The ratio of the oxidizing (halogenating) agent relative to zeaxanthin can vary between a catalytic amount to 2 molar equivalents. The term "catalytic amount" refers to an amount of the oxidizing agent added that is less than the corresponding stoichiometric quantity of the zeaxanthin used in the reaction. The term "stoichiometric" refers to the use of an equivalent mole ratio or amount of a reagent relative to a selected substrate, molecule or compound in a reaction.

The ratio of the oxidizing (halogenating) agent can vary from a catalytic amount used, as in the case of iodine, sodium iodide or sodium bromide, to about 2 molar equivalents when N-bromosuccinimide or pyridinium bromide per bromide is employed.

Typically the reaction is carried out in a two-phase system with an inert organic solvent layer and an aqueous layer. Typically, the organic layer can be any inert solvent or solvent mixtures, but preferably, chlorinated solvents such as chloroform or methylene chloride are used.

The ratio of the zeaxanthin to the organic solvent can vary from 1:10 to 1:500, depending on the reaction conditions. Preferably, the ratio of zeaxanthin to the organic solvent is about from 1:10 to about 1:200.

The reaction is conducted in the presence of salts of chloric or bromic acids in an aqueous solution. The reaction may also be performed using salts of metal bromate or metal chlorate or mixtures of chloric and bromic acids and metal bromate and chlorate salts thereof. Preferably, the aqueous solution is prepared by dissolving sodium or potassium chlorate or bromate in water. Also preferably, the aqueous solution can be prepared by a mixture of potassium or sodium bromate and potassium or sodium bromide in water.

The ratio of the water to the salt mixture is determined by solubility of the salt employed and the optimized concentration for efficient reaction throughput.

The ratio of the chlorate or bromate salts to zeaxanthin can vary from about 1:1 to about 50:1, preferably from about 1:1 to about 25:1. The ratio of bromide salts or iodide salts can be catalytic to 1:10.

The reaction may be conducted in solution at an aqueous pH in the range from about pH=1 to pH=9, preferably between pH=2 to pH=8. The pH of the solution may be adjusted with a base or with an acid. Preferably, the base is selected from the group consisting of sodium hydroxide, potassium hydroxide, sodium carbonate, potassium carbonate, sodium bicarbonate, potassium bicarbonate and mixtures thereof. The acid is selected from the group consisting of hydrochloric acid, hydrobromic acid, hydroiodic acid, acetic acid, sulfuric acid, phosphoric acid and mixtures thereof. Preferably, the acid is hydrochloric acid or sulfuric acid. Aqueous metal sulfites solutions may also be used to quench the reaction containing salts of metal bromate. Preferably, aqueous solutions of sodium sulfite may be used to quench the reaction mixture.

The temperature of the reaction may vary from −78° C. to 50° C. Preferably the reaction is conducted from about −60° C. to about 30° C. and most preferably from about −30° C. to about 30° C.

In another embodiment of the present invention, the conversion can also be carried out in two sequential steps. In the first step, allylic oxidation from the methylene to the corresponding allylic alcohol or halide can be performed followed by the subsequent conversion to the corresponding enone. Preferably, the allylic alcohol or allylic halide intermediate is prepared by reaction first with N-bromosuccinimide or similar halogenating agents in water followed by the reaction of the intermediate with a base. Preferably, the base is an amine base. Most preferably, the base is tertiary amine base such as N,N-diisopropylethylamine. The reaction can also be carried out effectively using an aqueous layer either neutral or basic.

Without being bound by any theory, it is believed that contacting the alcohol or halide with an aqueous solution of the bromate or chlorate salt under slightly acidic conditions, in the presence of a halogenating agent, results in the desired product.

Additional objects, advantages, and novel features of this invention will become apparent to those skilled in the art upon examination of the following examples thereof, which are not intended to be limiting.

EXAMPLE 1

This example illustrates the one-step conversion of zeaxanthin to astaxanthin using N-bromosuccinimide and sodium chlorate.

In a 50 ml one necked round-bottomed flask equipped with a magnetic stir bar under nitrogen was charged zeaxanthin (120 mg, 70% pure), chloroform (20 ml) and a solution of aqueous sodium chlorate (0.3 g in 10 ml water). The resulting slurry is stirred at 25° C. and the pH of the solution is adjusted to pH=8 with sodium bicarbonate.

In a separate 25 ml round-bottomed flask is charged N-bromosuccinimide (40 mg) and chloroform (5 ml). The N-bromosuccinimide solution is added to the vigorously stirred zeaxanthin solution over a period of 4–6 hours. The color of the reaction mixture turns bright red.

TLC (thin layer chromatography) indicated good formation of the desired astaxanthin product.

Upon completion of the reaction, the phases are separated and the organic layer is washed with water (2×10 ml). The organic layer is dried over magnesium sulfate and concentrated 10 fold. The concentrate is placed upon dry silica gel and eluted with 5% acetone in chloroform. The first fractions contain the purified astaxanthin, which was identified by comparison with commercially available samples.

In a similar manner obtaining the similar yields, potassium bromate can be employed in place of sodium chlorate in the above process.

EXAMPLE 2

This example illustrates the one-step conversion of zeaxanthin to astaxanthin using pyridinium tribromide and sodium chlorate.

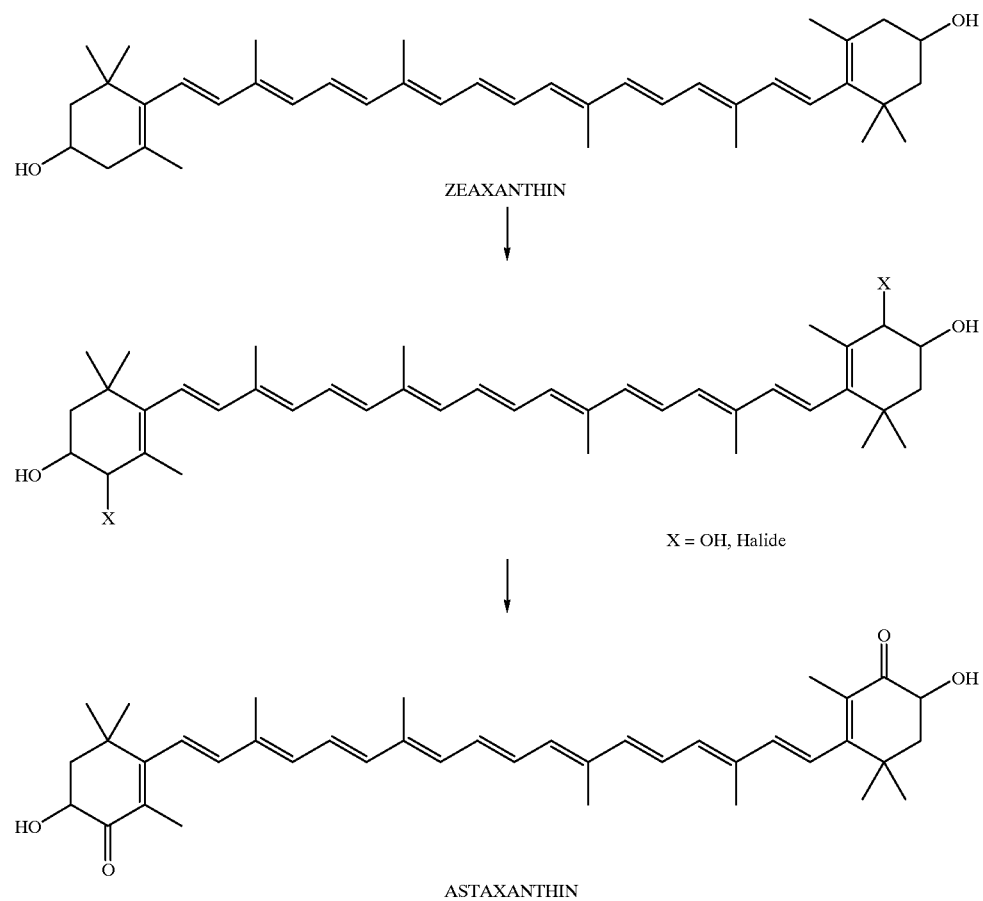

ZEAXANTHIN

X = OH, Halide

ASTAXANTHIN

In a 50 ml one necked round bottom flask equipped with a magnetic stir bar under nitrogen was charged zeaxanthin (50 mg, 70% pure), chloroform (10 ml) and a solution of aqueous sodium chlorate (0.15 g in 5 ml water). The stirred mixture is adjusted to a pH=6.

The resulting mixture is stirred vigorously and solid pyridinium tribromide (30 mg, 0.094 mmoles) is added slowly to the mixture over 3 hours. The reaction mixture quickly turned red and remained a red solution throughout the addition.

TLC after 3 hours indicated good conversion to astaxanthin. Upon completion of the reaction, the phases are separated and the organic layer is washed with water (2×10 ml). The organic layer is dried over magnesium sulfate and concentrated 10 fold. The concentrate is placed upon dry silica gel and eluted with 5% acetone in chloroform. The first fractions contain the purified astaxanthin, which was identified by comparison with commercially available samples.

EXAMPLE 3

This example illustrates the two-step conversion of zeaxanthin to astaxanthin using N-bromosuccinimide, acetic acid and sodium chlorate.

In a 100 ml one necked round-bottomed flask equipped with a magnetic stir bar under nitrogen was charged zeaxanthin (100 mg, 90% pure), and chloroform (50 ml, ethanol free). To this mixture was added glacial acetic acid (300 mg).

The reaction mixture was cooled to −60° C. and a solution of N-bromosuccinimide (40 mg in 5 ml of chloroform) was slowly added. After the addition, the reaction mixture was warmed to −25° C. and N, N-diisopropylethylamine (0.5 gm) was added all at once. The reaction mixture lightens considerably.

The mixture was allowed to warm to 25° C. and the chloroform solution was washed with water and evaporated on a rotary evaporator. The residue was dissolved in 15 ml of 10% methanolic potassium hydroxide and stirred at room temperature for 20 minutes.

Chloroform (25 ml) was added and the solution was extracted successively with IN HCl (5 ml), aqueous sodium bicarbonate (5 ml) and water (5 ml).

Rotary evaporation of the solution produced a residue containing a mixture of isomeric tetrahydroxy compounds which was used directly in the subsequent oxidation reaction. The tetrahydroxy compounds were identified by TLC and NMR. The compounds were identical to the material obtained from the reduction of astaxanthin with sodium borohydride.

The above residue was dissolved in chloroform (20 ml) and added to a 100 ml round bottomed flask containing sodium chlorate (300 mg) in water (10 ml). The pH of the solution was adjusted to pH=3 with dilute sulfuric acid.

The resulting mixture was vigorously stirred at 25° C. and a solution of N-bromosuccinimide (20 mg) in chloroform (5 ml) was added slowly over 3 hours. The resulting mixture turned dark red and astaxanthin was formed as determined by TLC comparison with authentic material.

Upon completion of the reaction, the phases are separated and the organic layer is washed with water (2×10 ml). The organic layer is dried over magnesium sulfate and concentrated 10 fold. The concentrate is placed upon dry silica gel and eluted with 5% acetone in chloroform. The first fractions contain purified astaxanthin, which was identified by comparison with commercially available samples.

EXAMPLE 4

This example illustrates the conversion of zeaxanthin to astaxanthin using potassium bromate and potassium bromide in a water-chloroform mixture.

Dissolve 50 mg of a natural extract containing 62% zeaxanthin in 10 ml of chloroform and cool with an ice bath. In a separate flask, prepare a solution of 300 mg potassium bromate in 10 ml of water and a solution of 214 mg potassium bromide in 5 ml of water. These two solutions are mixed together and then acidified with 1 ml of 2% v/v sulfuric acid. This solution is poured immediately into the reaction flask containing the solution of zeaxanthin.

The reaction is substantially complete after 30 minutes after which 225 mg of sodium sulfite in 5 ml of water was added to quench the reaction. The mixture is filtered to remove unreacted material and the solvent phases were separated. The organic phase was washed with water, separated and dried over magnesium sulfate. The resulting solution is poured through 1 gram of silica-alumina grade 335 and the solid is washed with 10 ml of chloroform. The resulting solution was evaporated to produce a solid. This solid was recrystallized by dissolving in the minimal amount of acetone and adding three volumes of hexane. Upon cooling to −5° C., a solid formed. This was filtered off to yield 9 mg of astaxanthin product (30%).

EXAMPLE 5

This example illustrates the conversion of zeaxanthin to astaxanthin using sodium bromate, potassium bromide and sulfuric acid.

Zeaxanthin (6.24 gm, 11 mmole) was slurried in 110 ml of chloroform under nitrogen and cooled on ice. To this stirred mixture, was added a solution of 6.14 gm (51.6 mmole) sodium bromate in 35 ml of water and acidified with 1 ml of 50% sulfuric acid. The three phase mixture was cooled on ice and 4 ml of a solution containing 4.84 gm (32.1 mmole) of potassium bromide in 15 ml of water was added rapidly to begin the reaction. After 1 hour, 7 ml of 3 N sodium hydroxide was added and the mixture was stirred for 15 minutes. The mixture was filtered over celite and the phases were separated. The organic layer was washed with basic water and separated. The chloroform was removed under vacuum at around 40° C. until a thick slurry remained. Ethanol (90 ml) was added and the remaining chloroform was removed by vacuum distillation. The reaction mixture was cooled and the product collected by filtration to yield 1.78 grams (28.5% yield) astaxanthin.

EXAMPLE 6

This example illustrates the conversion of zeaxanthin to astaxanthin using sodium iodide, sodium chlorate and sulfuric acid.

Zeaxanthin (50 mg) was stirred in 20 ml of chloroform under nitrogen. To this stirred mixture, 200 mg of sodium chlorate and 50 mg of sodium iodide in 10 ml of water was added. The mixture was acidified slowly with 1 ml of 27% sulfuric acid. The reaction was stirred at room temperature. After 5 hours, a significant quantity of astaxanthin had formed. The reaction was worked up by addition of 1 ml of 40% sodium hydroxide, separation of the organic solution and evaporation to yield astaxanthin.

Those skilled in the art will appreciate that numerous changes and modifications may be made to the preferred embodiments of the invention and that such changes and modifications may be made without departing from the spirit of the invention disclosed herein. It is therefore intended that the appended claims cover all such equivalent variations as may fall within the true spirit and scope of the invention.

What is claimed is:

1. A method for preparing astaxanthin from zeaxanthin or 3,3',4,4'-tetrahydroxy-β-carotene, comprising contacting said zeaxanthin or 3,3',4,4'-tetrahydroxy-β-carotene with a halogenating agent in the presence of chloric or bromic acid or salts thereof.

2. The method of claim 1, wherein said halogenating agent is selected from the group consisting of N-bromosuccinimide, bromine, pyridinium tribromide, iodine, and mixtures thereof either added directly or generated in situ with a compound selected from the group consisting of sodium bromide, potassium bromide, sodium iodide and potassium iodide.

3. The method of claim 2 further comprising a reaction solvent system, wherein said reaction solvent is selected from the group consisting of an organic solvent and water.

4. The method of claim 3, wherein said organic solvent is chloroform.

5. The method of claim 4, wherein said halogenating agent is N-bromosuccinimide or pyridinium tribromide.

6. The method of claim 4, wherein said halogenating agent is generated in situ from a mixture of an oxidizing agent and a compound selected from the group consisting of potassium bromide, sodium bromide, sodium iodide and potassium iodide.

7. The method of claim 6, wherein said oxidizing agent is selected from the group consisting of bromic acid, chloric acid and salts thereof.

8. The method of claim 6, wherein the mixture is acidic.

9. The method of claim 8, wherein the mixture comprises a solution of sodium bromate and potassium bromide.

10. The method of claim 8, wherein the mixture comprises a solution of sodium iodine and sodium chlorate.

11. A method for preparing 3,3',4,4'-tetrahydroxy-β-carotene from zeaxanthin, comprising contacting said zeaxanthin with a halogenating agent to form a mixture followed by contacting said mixture with a base.

12. The method of claim 11, wherein said halogenating agent is N-bromosuccinimide and said base is an amine base.

13. The method of claim 11, wherein said halogenating agent is selected from the group consisting of N-bromosuccinimide, bromine, pyridinium tribromide, iodine, and mixtures thereof either added directly or generated in situ with a compound selected from the group consisting of sodium bromide, potassium bromide, sodium iodide and potassium iodide.

14. The method of claim 11 further comprising a reaction solvent system, wherein said reaction solvent is selected from the group consisting of an organic solvent and water.

15. The method of claim 14, wherein said organic solvent is chloroform.

16. The method of claim 14, wherein said halogenating agent is N-bromosuccinimide and said amine base is N,N-diisopropylethylamine.

17. A method for preparing astaxanthin from 3,3',4,4'-tetrahydroxy-β-carotene, comprising contacting said 3,3',4,4'-tetrahydroxy-β-carotene with a mixture comprising a halogenating agent and an acid selected from the group consisting of bromic acid, chloric acid and salts thereof.

18. The method of claim 17 further comprising a reaction solvent system, wherein said reaction solvent is selected from the group consisting of an organic solvent and water.

19. The method of claim 18, wherein said organic solvent is chloroform.

20. The method of claim 17, wherein said halogenating agent is generated in situ from a mixture of an oxidizing agent and a compound selected from the group consisting of potassium bromide, sodium bromide, sodium iodide and potassium iodide.

21. The method of claim 20, wherein the oxidizing agent is selected from the group consisting of bromic acid, chloric acid, and salts thereof.

22. The method of claim 20, wherein the mixture is acidic.

23. The method of claim 22, wherein the mixture comprises solutions of sodium bromate and potassium bromide.

24. The method of claim 22, wherein the mixture comprises solutions of sodium iodine and sodium chlorate.

25. The method of claim 17, wherein the halogenating agent is N-bromosuccinimide.

* * * * *